United States Patent
Miyake et al.

(10) Patent No.: US 7,684,851 B2
(45) Date of Patent: Mar. 23, 2010

(54) BODY CAVITY INTERIOR OBSERVING APPARATUS

(75) Inventors: Yoichi Miyake, Sakura (JP); Tatsuo Igarashi, Chiba (JP); Harufumi Makino, Chiba (JP); Toshiya Nakaguchi, Funabashi (JP); Hiroshi Fujita, Saitama (JP)

(73) Assignee: Fujinon Corporation, Saitama-Shi (JP)

( * ) Notice: Subject to any disclaimer, the term of this patent is extended or adjusted under 35 U.S.C. 154(b) by 273 days.

(21) Appl. No.: 11/707,143

(22) Filed: Feb. 16, 2007

(65) Prior Publication Data
US 2007/0232863 A1 Oct. 4, 2007

(30) Foreign Application Priority Data
Feb. 21, 2006 (JP) ............................. 2006-044378

(51) Int. Cl.
*A61B 5/05* (2006.01)
*A61B 1/00* (2006.01)
*A61B 1/06* (2006.01)
*A61B 6/00* (2006.01)
*H04N 7/18* (2006.01)

(52) U.S. Cl. .................. 600/424; 600/103; 600/114; 600/173; 600/476; 348/65

(58) Field of Classification Search ............... 600/424, 600/426, 427, 103, 114, 117, 173, 476; 348/65
See application file for complete search history.

(56) References Cited

U.S. PATENT DOCUMENTS

| 5,774,599 A | * | 6/1998 | Muka et al. | ............... 382/254 |
| 5,836,869 A | | 11/1998 | Kudo et al. | |
| 6,036,637 A | | 3/2000 | Kudo | |
| 2003/0105400 A1 | * | 6/2003 | Yawata et al. | ............... 600/437 |

FOREIGN PATENT DOCUMENTS

| JP | 8-164148 A | 6/1996 |
| JP | 09-266882 | 10/1997 |
| JP | 9-266882 A | 10/1997 |

* cited by examiner

*Primary Examiner*—Eric F Winakur
*Assistant Examiner*—Michael T Rozanski
(74) *Attorney, Agent, or Firm*—Birch, Stewart, Kolasch & Birch, LLP (57) ABSTRACT

According to a body cavity interior observing apparatus of the present invention, a non-tracked region to be displayed can be switched between a first non-tracked region and a second non-tracked region which is larger than the first non-tracked region, and in a search for an affected area in which it is preferable to track a treating instrument in order to consistently align the position of treating instrument to the central part of the screen, the first non-tracked region having a smaller non-tracked region is selected, while in a treatment of an affected area in which a treating instrument is moved in a wide range of area, the second non-tracked region having a larger non-tracked region is selected, thereby an appropriate monitor screen can be provided in searching for an affected area and in treating an affected area.

3 Claims, 5 Drawing Sheets

BODY CAVITY INTERIOR OBSERVING APPARATUS

BACKGROUND OF THE INVENTION

1. Field of the Invention

The present invention relates to a body cavity interior observing apparatus, in particular, a body cavity interior observing apparatus for performing various treatments while an image of a body cavity interior of an object to be examined is displayed on a monitor.

2. Description of the Related Art

A laparoscopic apparatus is a body cavity interior observing apparatus, and after a trocar (penetrating instrument) is stabbed into the body cavity interior through a abdominal part surface of a patient, and a laparoscope inserting section is inserted into the body cavity interior with help of the trocar as a guide, the laparoscopic apparatus is used to perform various treatments such as a treatment of adhesion while displaying a presence or absence of adhesion of a body cavity interior, or an image of a body part of an object to be examined such as ovarian tumor and hysteromyoma on a monitor. The laparoscope is held by a movable holder which is mounted to a fixing section to be maintained in a fixed state in clinical practice (for example, see Japanese Patent Application Laid-Open No. H8-164148).

In clinical practices that use such a laparoscopic apparatus, in order to observe a body part of an object to be examined which is actually treated at the central part of a monitor screen, a position of a distal end portion of a treating instrument which is located inside of a body cavity is detected so that the distal end portion of the treating instrument can be tracked to constantly align the position of the distal end portion to the central part of an image displayed on a monitor. The tracking mechanism described in the Japanese Patent Application Laid-Open No. H8-164148 includes a magnetic three-dimensional position sensor which is mounted to a part of laparoscope located outside of a patient's body. The magnetic three-dimensional position sensor includes a magnet source which is mounted to the laparoscope, and a magnetic sensor which is mounted to a treating instrument, and is configured to obtain position information of the distal end portion of the treating instrument located inside of a body cavity by calculating the position of the distal end portion of the treating instrument, which is used for a treatment and is located in the body, from a mount position of the magnetic sensor outside of the body by using a rotation/translation coordinate transformation.

In a laparoscopic apparatus having the tracking mechanism, as the treating instrument moves, an observation image which is displayed on a monitor screen continuously moves, resulting in that, every time the treating instrument is moved for operations of various treatments and examinations of an affected area, the monitor screen wobbles, which may be troublesome for a practitioner in observing or treating of an affected area.

Japanese Patent Application Laid-Open No. H9-266882 discloses a laparoscopic apparatus which solves such a trouble. In the laparoscopic apparatus, a monitor screen is divided into a central non-tracked region and an outer tracked region which surrounds the non-tracked region, so that when a treating instrument moves into the tracked region out of the non-tracked region, a tracking function is turned on to move an image of the treating instrument to the central part of the monitor screen, while when the treating instrument is located in the non-tracked region, the tracking function is turned off to prevent the wobble of the observation image.

SUMMARY OF THE INVENTION

However, the laparoscopic apparatus disclosed in the above Japanese Patent Application Laid-Open No. H9-266882 is convenient since the screen does not wobble in treating an affected area by moving a treating instrument in a wide range area because the size of the non-tracked region is larger than that of the monitor screen, but the laparoscopic apparatus is inconvenient in an operation to search for the affected area because it is preferable to track the treating instrument to consistently align the position of the treating instrument to the central part of the screen. This trouble can be solved by switching the entire screen to the tracked region, but this makes the tracking function effective to every subtle movement (vibration) of the treating instrument and so the monitor screen slightly moves all the time, which makes it difficult for a practitioner to watch the image.

The present invention was made in view of the above described background, and one object of the present invention is to provide a body cavity interior observing apparatus which can provide an appropriate monitor screen both in searching for an affected area and in treating an affected area.

In order to achieve the above object, a first aspect of the present invention provides a body cavity interior observing apparatus, comprising: a treating instrument which is inserted into a body cavity interior of an object to be examined by using a penetrating instrument as a guide; an observing section which is mounted to an opening portion of a body wall of the object; a monitor which displays an image of the body cavity interior picked up by the observing section; a marker position detecting device for detecting a position of a marker attached to the treating instrument or the penetrating instrument from the image which shows the body cavity interior picked up by the observing section; and a tracking device for tracking the position of the marker detected by the marker position detecting device to align the position of the marker to a central part of a screen of the monitor, wherein a screen of the monitor is divided into a tracked region and a non-tracked region, and when the marker is located in the non-tracked region, the tracking device does not work, and the non-tracked region to be displayed is switched between a first non-tracked region which is positioned generally at the central part of the screen of the monitor and a second non-tracked region which is larger than the first non-tracked region.

According to the first aspect of the present invention, the screen of the monitor is divided into a tracked region and a non-tracked region, and also, the non-tracked region to be displayed can be switched between a first non-tracked region which is positioned generally at the central part of the screen of the monitor and a second non-tracked region which is larger than the first non-tracked region.

In a search for an affected area in which it is preferable to track a treating instrument in order to consistently align the position of treating instrument to the central part of the screen, the first non-tracked region having a smaller non-tracked region is selected. Thus, when the marker goes out of the smaller first non-tracked region, the marker is located in a tracked region, thereby a tracking function is turned on for any slight movement of the marker. This makes it possible to consistently align the position of the treating instrument to the central part of the screen in a search for an affected area. The tracking function is not turned on for subtle movements and vibrations of the treating instrument in the first non-tracked region. As a result, the monitor screen does not move, which provides a screen that is easy to watch for a practitioner. To the contrary, in a treatment of an affected area in which a treating instrument is moved in a wide range of area, the second non-tracked region having a larger non-tracked region is selected. Thus, even when a marker moves in the second non-tracked region having a larger area, the screen does not move, which makes the treatment of the affected area easy to perform for a practitioner. As a result, a body cavity interior observing apparatus of the present invention can provide an appropriate monitor screen in searching for an affected area and in treating an affected area.

A second aspect of the present invention provides the body cavity interior observing apparatus according to the first aspect, wherein the tracking device includes: a trimming device for trimming an image to obtain a predetermined region so that the position of the marker which is detected by the marker position detecting device is positioned at the central part of the screen of the monitor; and a magnifying device for magnifying the predetermined region trimmed by the trimming device at a predetermined magnification rate to be displayed on the monitor.

According to a body cavity interior observing apparatus of the present invention, a non-tracked region to be displayed can be switched between a first non-tracked region and a second non-tracked region which is larger than the first non-tracked region, and in a search for an affected area in which it is preferable to track a treating instrument in order to consistently align the position of treating instrument to the central part of the screen, the first non-tracked region having a smaller non-tracked region is selected, while in a treatment of an affected area in which a treating instrument is moved in a wide range of area, the second non-tracked region having a larger non-tracked region is selected, thereby an appropriate monitor screen can be provided in searching for an affected area and in treating an affected area.

DETAILED DESCRIPTION OF THE PREFERRED EMBODIMENTS

Now, preferable embodiments of a body cavity interior observing apparatus according to the present invention will be explained below with reference to the accompanying drawings.

Figure 1:
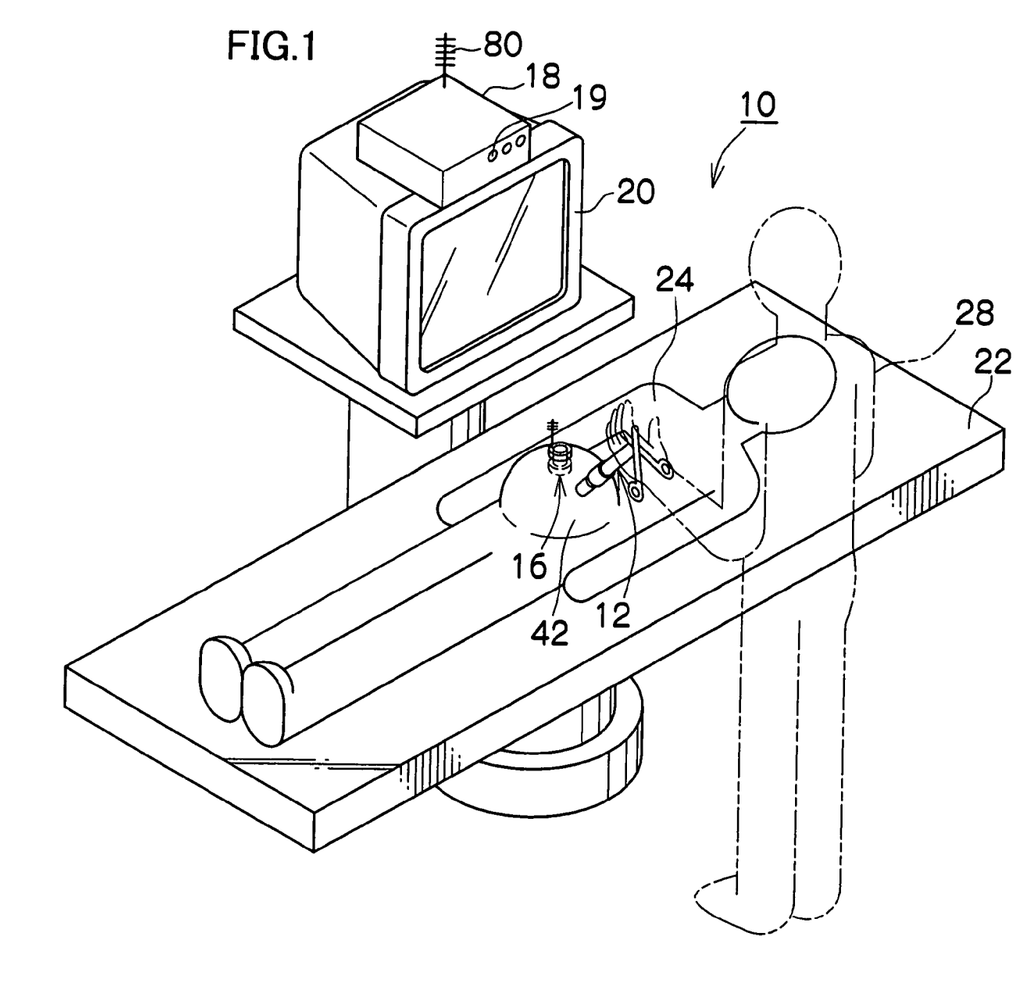
FIG. 1 is a system configuration diagram of a body cavity interior observing apparatus having an observation unit which integrally includes an observation optical system therein.
Figure 2:
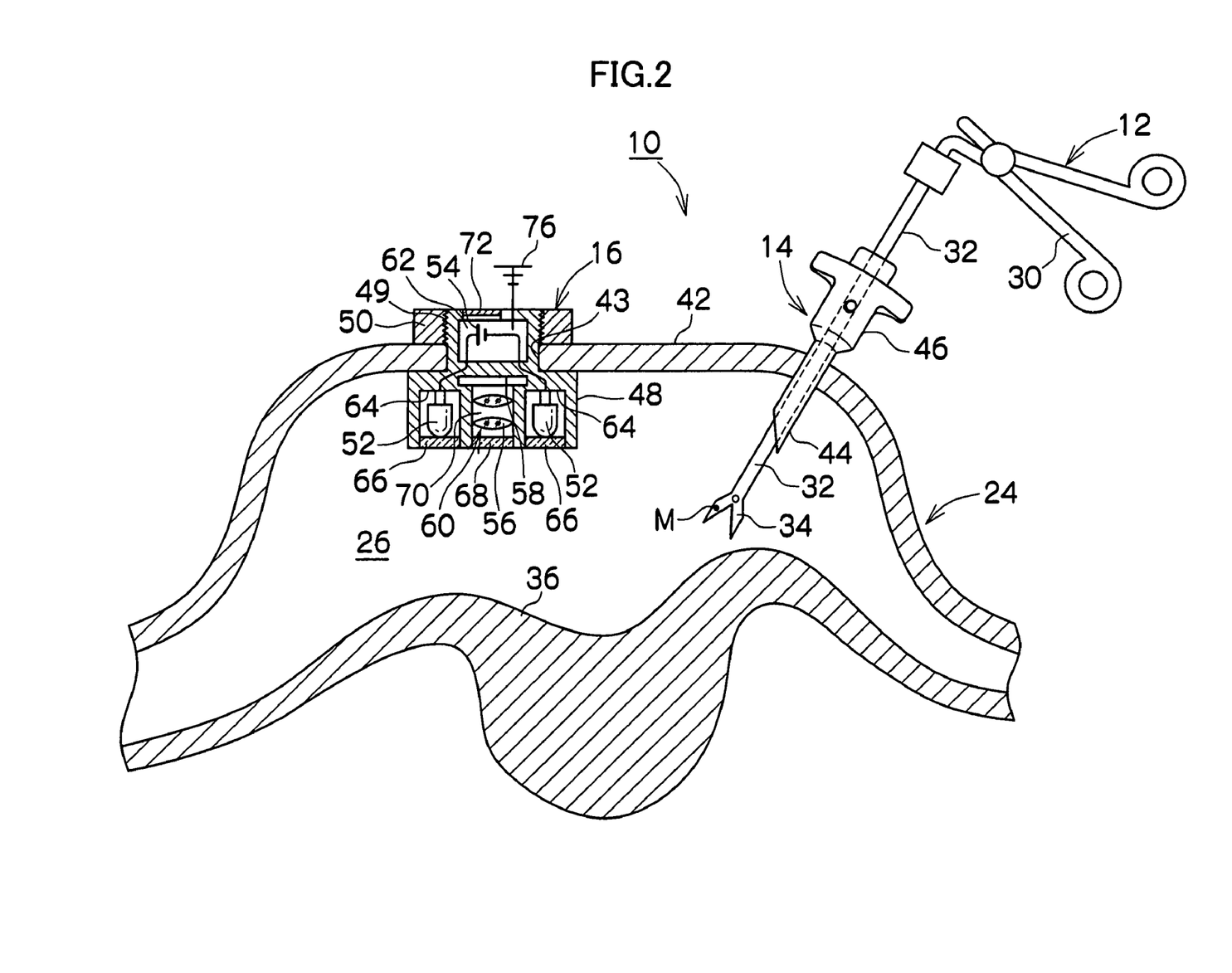
FIG. 2 is a diagram illustrating a clinical situation using the body cavity interior observing apparatus of FIG. 1.

FIG. 1 is a system configuration diagram of an embodiment of a body cavity interior observing apparatus 10 of the present invention, and FIG. 2 is a diagram illustrating a clinical situation using the body cavity interior observing apparatus 10.

As shown in FIG. 1 and FIG. 2, the body cavity interior observing apparatus 10 includes a treating instrument 12, a trocar (penetrating instrument) 14, an observation unit (observing section) 16, a video signal processor 18, and a monitor 20. Instead of the observation unit 16, an endoscope or a rigid endoscope which picks up an image of a body cavity interior may be used as an observing section.

The treating instrument 12 is used to treat an affected area in a body cavity 26 of an object to be examined 24 who is lying on an operating table 22, and is provided with an operating section 30 which is operated by an operator 28. In the treating instrument 12, an inserting section 32 is connected to a distal end of the operating section 30, and a forceps 34 is provided to a distal end of the inserting section 32.

The inserting section 32 of the treating instrument 12 is, as shown in FIG. 2, inserted into the body cavity 26 by using a trocar 14 as a guide, with the trocar 14 being stabbed through a surface of an abdominal part 42 of the object 24. The trocar 14 includes a metallic hollow tube 44 having a sharpened distal end, and a flexible holding tube 46 which is provided at a proximal end of the hollow tube 44. The trocar 14 is inserted into the body cavity 26 by the operator 28 who holds the holding tube 46 and stabs the trocar 14 through the abdominal part 42 with directing the sharpened distal end of the hollow tube 44 downward as the forefront thereof and thereby the hollow tube 44 is inserted in the body cavity 26.

The observation unit 16 is, as shown in FIG. 1, formed into a generally cylindrical shape, and is fixed to an opening part 43 which is formed by cutting the abdominal part 42 near the position stabbed by the trocar 14. The observation unit 16 includes, a unit body 48 which is formed into a generally cylindrical shape as shown in FIG. 2, and a nut section 50 which is threadedly engaged with a male screw part 49 of the unit body 48 to sandwich and press the abdominal wall (abdominal skin) between and against the unit body 48. The sandwich and press allows the observation unit 16 to be fixed to the opening part 43.

The unit body 48 includes a plurality of LEDs (light emitting diode) 52, a battery 54, an observation optical system 60 having a lens 56 and a CCD (charge-coupled device) 58, and a video signal transmitting section 62 for wirelessly transmitting video signals, therein. The plurality of LEDs 52 are arranged along the circumference of an identical circle about the central axis of the unit body 48 with an equal space therebetween. A receiving recess 64 for receiving the LEDs 52 is sealed by a plate 66 such as a transparent plate or a light scattering plate. The observation optical system 60 is disposed so that the optical axis thereof is aligned with the central axis of the unit body 48. A transparent plate 68 is disposed in front of the lens 56 of the observation optical system 60, which seals the storage recess 70 of the observation optical system 60.

Figure 3:
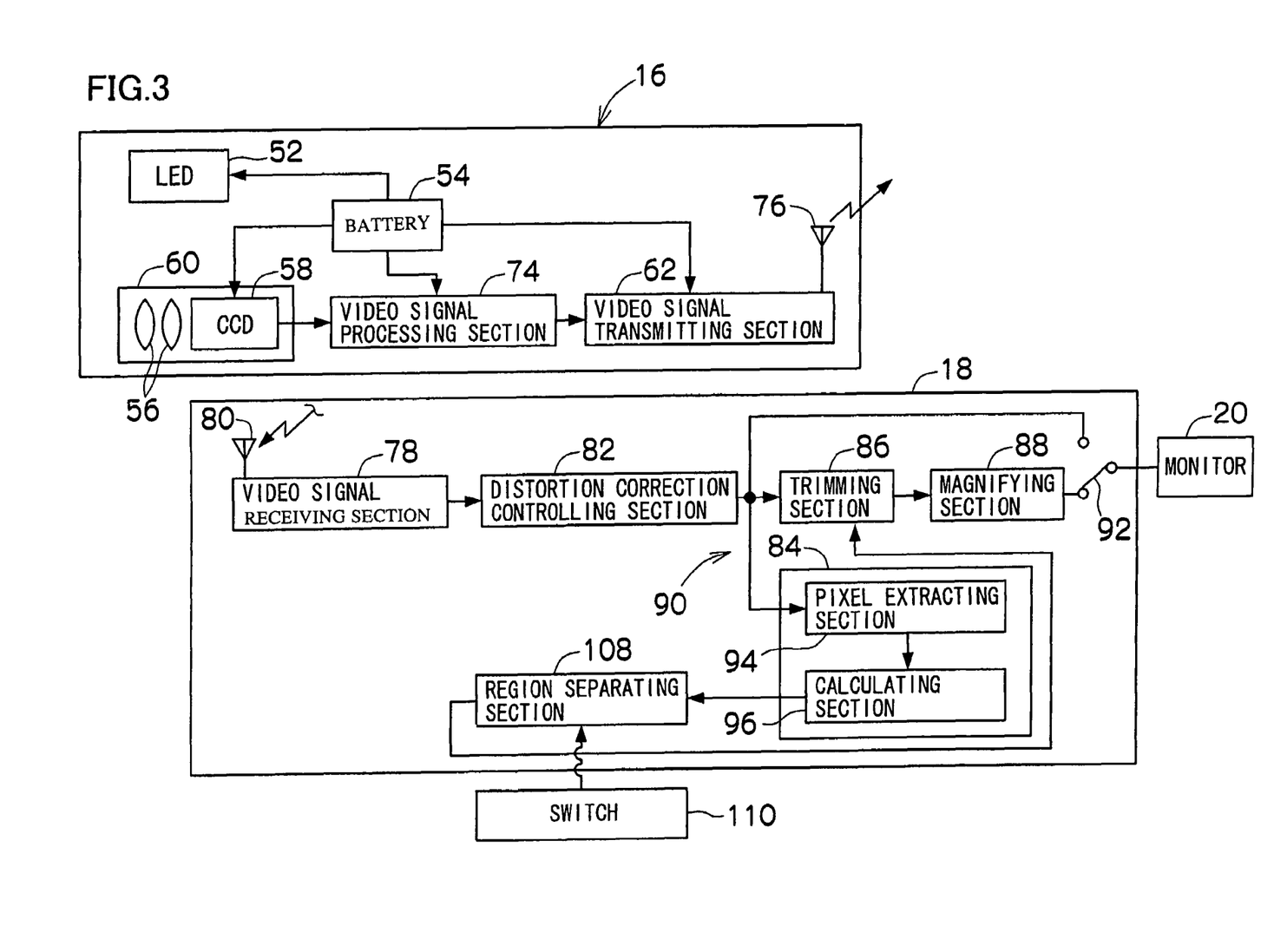
FIG. 3 is a block diagram showing a structure of the body cavity interior observing apparatus of FIG. 1.

The battery 54 is a button cell for a smaller size and weight of the unit. The battery 54 can be replaced with a new one after a cap 72 which is removably mounted to the upper surface of the unit body 48 is removed. The battery 54 supplies power to the LEDs 52, the CCD 58, and the video signal transmitting section 62 as shown in FIG. 3, and also supplies power to a video signal processing section 74 which processes the output signal from the CCD 58 into a video signal. The video signal processing section 74 is also built in the unit body 48 shown in FIG. 2.

According to the observation unit 16 having a configuration described above, the LEDs 52 illuminate an object to be observed 36, so that the optical image of the object to be observed is focused on the CCD 58 via the lens 56. The output signal from the CCD 58 is processed by the video signal processing section 74 into a video signal which is transmitted to the video signal processor 18 shown in FIG. 1 via an antenna 76 of the video signal transmitting section 62. That is, the observation unit 16 achieves the functions for illuminating, picking up images, and transmitting video signals by using the built-in battery 54.

The video signal transmitted to the video signal processor 18 is, as shown in FIG. 3, received by an antenna 80 of a video signal receiving section 78. The received video signal is, after the distortion of the lens 56 is corrected by a distortion correction controlling section 82, output to a marker tracking controlling section 90 which includes a marker position detecting section (a marker position detecting device) 84, a trimming section (a trimming device) 86, and a magnifying section (a magnifying device) 88.

Now, the marker tracking controlling section 90 will be explained below.

The observation optical system 60 of the observation unit 16 shown in FIG. 2 is the one which has a large field of view for observation over the entire body cavity 26, since the observation unit 16 is fixed to the opening portion of the body wall 43. However, if the entire region, the image of which is picked up by the observation optical system 60 having a large field of view for observation (for example, a view angle of 170 degree), is displayed on the monitor 20, there is a problem that the image of the site near the distal end portion of the treating instrument or trocar 14, which is the point the operator truly needs to observe, is displayed as a small region.

In order to avoid the problem, as shown in FIG. 2, a marker M having a color which is completely different from the body color (for example: green) is attached to the forceps 34 of the treating instrument 12. In an image processing by a marker tracking controlling section 90, the position of the marker M is detected by the marker position detecting section 84 of FIG. 3. Next, the processed image is trimmed to obtain a predetermined region by the trimming section 86 so that the marker M is positioned at the central part of the screen of the monitor 20. Then, the image region is magnified at a predetermined magnification rate by the magnifying section 88 to be displayed on the monitor 20. The magnification rate is adjusted by operating a magnification rate adjusting knob 19 of the video signal processor 18. The image processing as described above allows the image of the site the operator truly needs to observe to be widely displayed on the monitor 20, thereby the problem in using an observation optical system having a large field of view for observation can be eliminated. That is, since the observation optical system can be used while being fixed to the opening portion of the body wall 43 without any operation of the observation unit 16 by an operator, the number of operators can be reduced without any disadvantage for clinical practices. Even if the position of the marker M is changed by an operation of the treating instrument 12, since the marker position detecting section 84 consistently tracks the marker M, the image near the marker M can be magnified to be observed at all time. The marker M may be attached to the distal end of the trocar 14.

The video signal processor 18 of the embodiment includes an alteration switch 92. The alteration switch 92 selectively switches the video signal to be output to the monitor 20 between the video signal only after distortion correction and the video signal magnified after the automatic tracking of the marker M. When the latter signal is selected, an image near the marker M is magnified and observed on the monitor 20, while the former signal is selected, an image of the entire region which is picked up by the observation optical system 60 having a large field of view can be observed on the monitor 20, which is convenient in understanding the position of the forceps 34 of the treating instrument 12 relative to the entire body cavity 26.

Meanwhile, the marker position detecting section 84 of the body cavity interior observing apparatus 10 of the embodiment includes a pixel extracting section 94, and a calculating section 96.

The pixel extracting section 94 extracts a pixel group which has the same color as that of the green marker M attached to the treating instrument 12 from the image showing the body cavity interior which is picked up by the observation unit 16. The calculating section 96 then calculates the position of the center of gravity of the pixel group as the position of the marker M. In this way, only the circuits of the pixel extracting section 94 and the calculating section 96 which are built in the marker position detecting section 84 enable a detection of the position of the marker M, thereby the distal end portion of the treating instrument 12 can be detected by a simple configuration without adding other machine apparatus.

Specifically, the pixel extracting section 94 extracts, as the pixel group, the pixels where the output values of the color components which are included in the green color of the marker M are larger than the output values of the color components which are not included in the green color of the marker M by a predetermined threshold or more, among the output values of R, G, B which are output from the CCD 58 of the observation unit 16 via the video signal transmitting section 62.

Next, a calculation example by the calculating section 96 will be explained below.

The center of gravity $C_g$ of the green color region can be obtained by the following formula, provided that the pixel value of the color c={r, g, b} in the coordinate (x, y) is f(x, y, c):

$$C_g = \begin{bmatrix} C_{g,x} \\ C_{g,y} \end{bmatrix} \qquad \text{[Formula 1]}$$

$$= \begin{bmatrix} \dfrac{\sum_{i=1}^{W/5}\sum_{j=1}^{H/5} 5i \cdot h_g(5i, 5j)}{\sum_{i=1}^{W/5}\sum_{j=1}^{H/5} h_g(5i, 5j)} & \dfrac{\sum_{i=1}^{W/5}\sum_{j=1}^{H/5} 5j \cdot h_g(5i, 5j)}{\sum_{i=1}^{W/5}\sum_{j=1}^{H/5} h_g(5i, 5j)} \end{bmatrix}^t ,$$

$$h_g(x, y) = \begin{cases} 1 & \text{if } f(x, y, g) > f(x, y, r) + t_{g,r} \text{ and} \\ & \quad f(x, y, g) > f(x, y, b) + t_{g,b} \\ 0 & \text{else} \end{cases}.$$

where t is transposition, and W and H are the number of pixels in the horizontal and vertical direction of laparoscope input images, respectively. The $t_{g,r}$ and $t_{g,b}$ are the threshold parameters used in detecting the green color. In calculating the center of gravity, in this system, the detection is performed for every five pixels in row and column directions in order to reduce the cost involved in the calculation. The detection, however, may be performed for every pixel.

Figure 4:
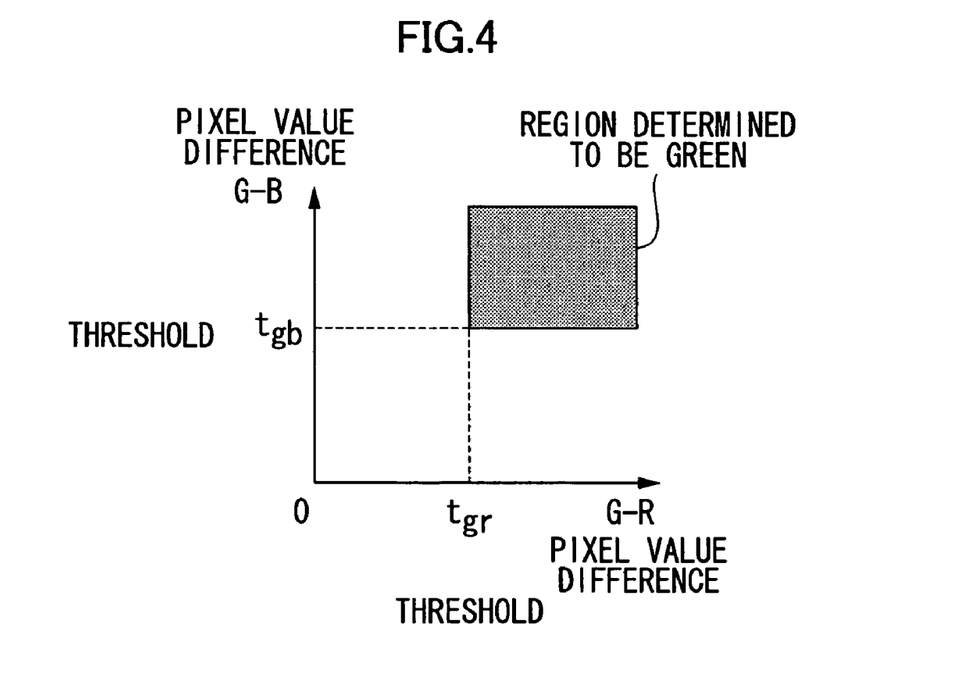
FIG. 4 is a diagram showing a green color region based on a set threshold parameter.

FIG. 4 shows a (determined) green color region based on the set threshold parameters $t_{g,r}$ and $t_{g,b}$. The horizontal axis of FIG. 4 represents a G-R pixel value difference, and the vertical axis represents a G-B pixel value difference.

When the marker M is set to be yellow, similarly, the center of gravity $C_y$ of the yellow color region can be obtained by the following formula:

$$C_y = \begin{bmatrix} C_{y,x} \\ C_{y,y} \end{bmatrix} \quad \text{[Formula 2]}$$

$$= \begin{bmatrix} \dfrac{\sum_{i=1}^{W/5}\sum_{j=1}^{H/5} 5i \cdot h_y(5i,5j)}{\sum_{i=1}^{W/5}\sum_{j=1}^{H/5} h_y(5i,5j)} & \dfrac{\sum_{i=1}^{W/5}\sum_{j=1}^{H/5} 5j \cdot h_y(5i,5j)}{\sum_{i=1}^{W/5}\sum_{j=1}^{H/5} h_y(5i,5j)} \end{bmatrix}^t,$$

$$h_y(x,y) = \begin{cases} 1 & \text{if } f(x,y,g) > f(x,y,b) + t_{g,b} \text{ and} \\ & \quad f(x,y,r) > f(x,y,b) + t_{r,b} \\ 0 & \text{else} \end{cases}.$$

where $t_{g,b}$, $t_{r,b}$ are the threshold parameters used in detecting the yellow color.

Figure 5:
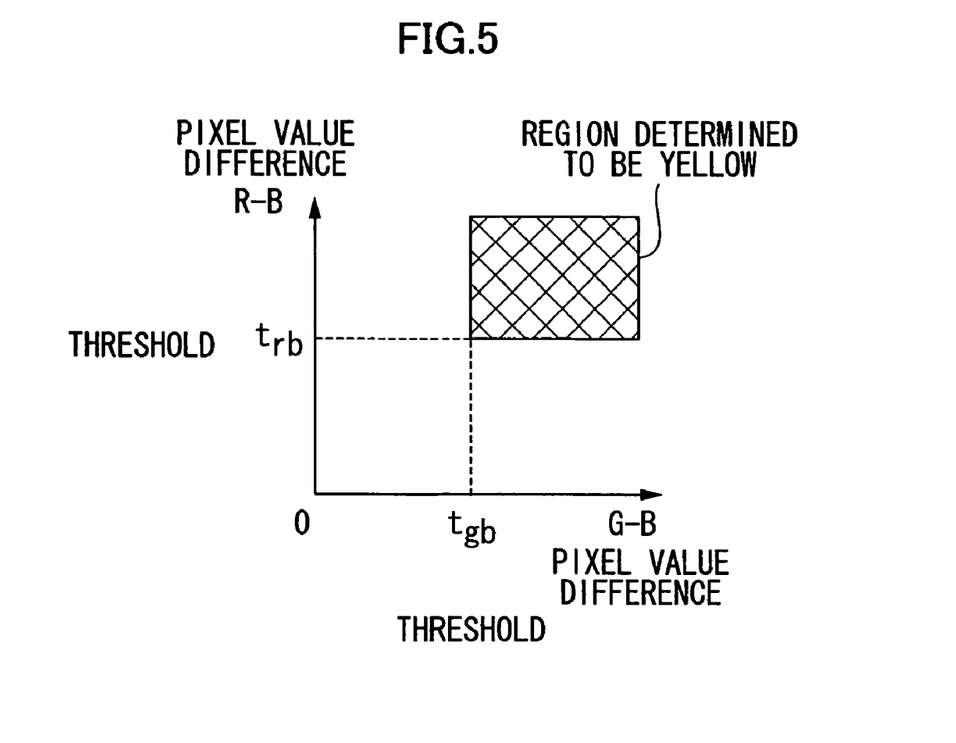
FIG. 5 is a diagram showing a yellow color region based on a set threshold parameter.

FIG. 5 shows a (determined) yellow color region based on the set threshold parameters $t_{g,b}$ and $t_{r,b}$. The horizontal axis of FIG. 5 represents a G-B pixel value difference, and the vertical axis represents a R-B pixel value difference.

As described above, since the calculating section 96 calculates the center of gravity for each color region having green color and yellow color respectively, even when two treating instruments 12 are simultaneously inserted, the positions of the distal ends of the two treating instruments 12 can be detected respectively.

Moreover, as described above, since the pixel extracting section 94 extracts, as the pixel group, the pixels where the output values of the color components which are included in the color of the marker M are larger than the output values of the color components which are not included in the color of the marker M by a predetermined threshold or more, among the output values of R, G, B which are output from the CCD 58 of the observation unit 16, the truly needed pixels, that is the color of the marker M, can be extracted.

Figure 6:
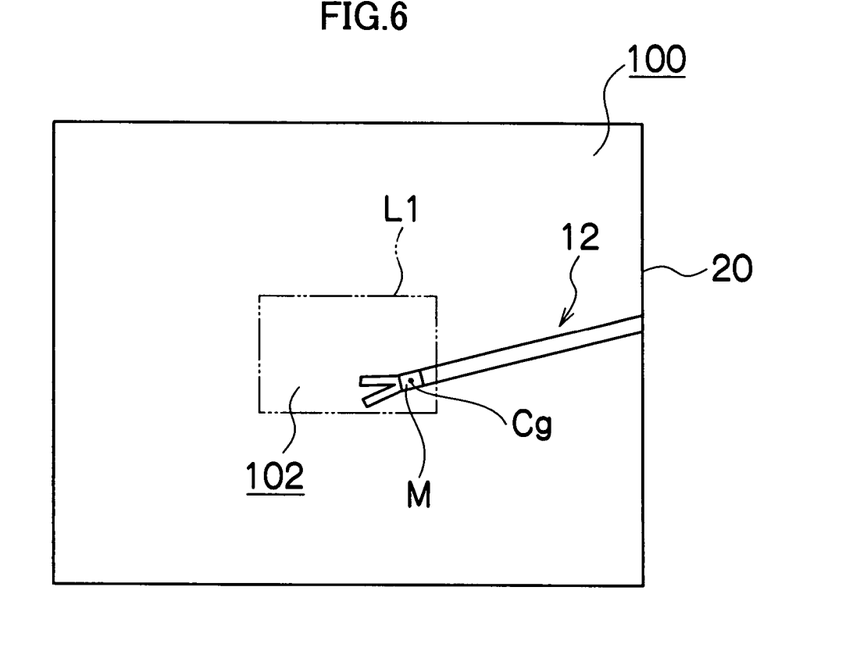
FIG. 6 is a diagram illustrating a monitor screen which shows a first non-tracked region having a smaller non-tracked region.
Figure 7:
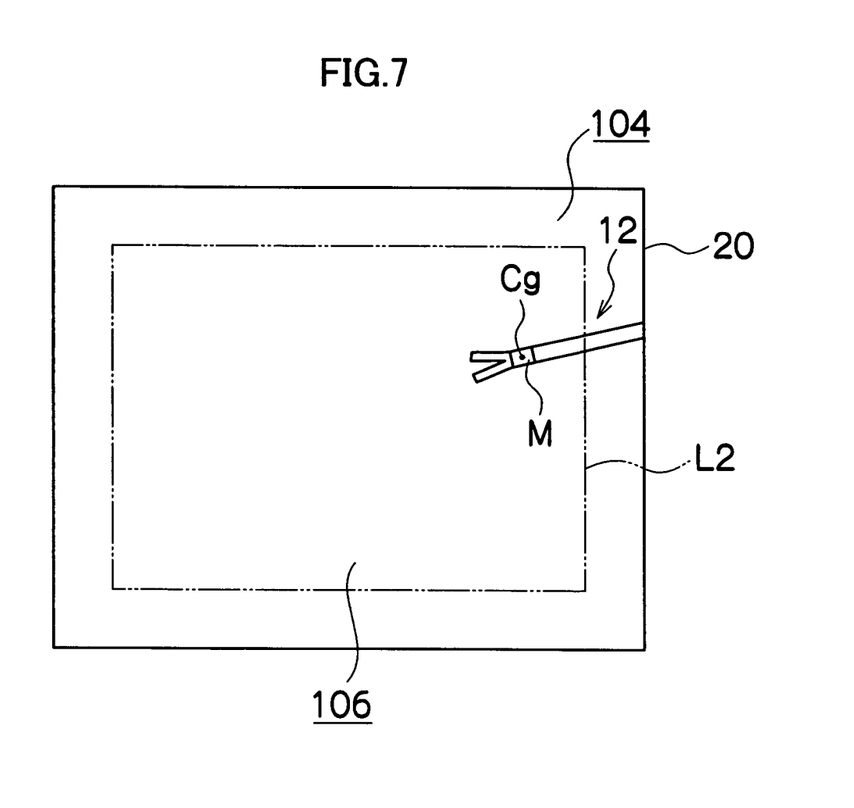
FIG. 7 is a diagram illustrating a monitor screen which shows a second non-tracked region having a larger non-tracked region.

Meanwhile, the video signal processor 18 is provided with a region separating section 108 which separates a screen of the monitor 20 into a tracked region 100 and a non-tracked region (a first non-tracked region) 102 as shown in FIG. 6, and also separates a screen of the monitor 20 into a tracked region 104 and a non-tracked region (a second non-tracked region) 106 as shown in FIG. 7. The non-tracked region 102 of FIG. 6 is a rectangular region which is surrounded by a boundary line L1 shown by a chain double-dashed line and is generally located at the center of the screen of the monitor 20, and the tracked region 100 is the strip region located outside of the non-tracked region 102. Similarly, the non-tracked region 106 shown in FIG. 7 is larger than the non-tracked region 102 shown in FIG. 6 and is a rectangular region surrounded by a boundary line L2 shown by a chain double-dashed line, and the tracked region 104 is the strip region located outside of the non-tracked region 106.

In the region separating section 108, depending on a selection signal from a manual switch 110, the first separated state shown in FIG. 6 or the second separated state shown in FIG. 7 is selected, and in either selected state, the trimming section 86 is controlled so that: when the center of gravity Cg of the marker portion M is located in the non-tracked region 102 or 106, the trimming section 86 is controlled to stop its function, and; when the center of gravity Cg of the marker portion M is located in the tracked region 100 or 104, the trimming section 86 is controlled to operate, so that the center of gravity Cg of the marker portion M is aligned to the central part of the screen of the monitor 20.

Next, actions of the body cavity interior observing apparatus 10 having the configuration described above will be explained below.

First, in a search for an affected area in which it is preferable to track the treating instrument 12 in order to consistently align the position of the treating instrument 12 to the central part of the screen of the monitor 20, the separated state with the non-tracked region 102 of FIG. 6 which has a smaller non-tracked region is selected by using the manual switch 110.

Thus, in searching for an affected area, when the marker portion M goes out of the non-tracked region 102 having a smaller region, the marker portion M is positioned in a tracked region 100, thereby a tracking function of the trimming section 86 is turned on for any slight movement of the marker portion M. This makes it possible to consistently align the position of the treating instrument 12 to the central part of the screen in searching for an affected area. The tracking function is not turned on for subtle movements and vibrations of the treating instrument 12 in the non-tracked region 102. As a result, the screen of the monitor 20 does not move due to the subtle movements and vibrations of the treating instrument 12, which provides a screen which is easy to watch for a practitioner.

Next, in a treatment of an affected area in which the treating instrument 12 is moved in a wide range of area, the separated state with the non-tracked region 106 of FIG. 7 which has a larger non-tracked region is selected by using the manual switch 110. Thus, even when the marker portion M moves in the non-tracked region 104 having a larger area, the screen does not move, which makes the treatment of the affected area easy for a practitioner.

Therefore, according to the body cavity interior observing apparatus 10 of the embodiment, an appropriate monitor screen can be provided in searching for an affected area and in treating an affected area.

What is claimed is:

1. A body cavity interior observing apparatus, comprising:
   a treating instrument which is inserted into a body cavity interior of an object to be examined includes a penetrating instrument as a guide;
   an observing section which is adapted to be mounted to an opening portion of a body wall of the object;
   a monitor which displays an image of the body cavity interior picked up by the observing section;
   a marker position detecting device for detecting a position of a marker attached to a distal end of the treating instrument from the image which shows the body cavity interior picked up by the observing section;
   a tracking device for tracking the position of the marker detected by the marker position detecting device to align the position of the marker to a central part of a screen of the monitor,
   a region separating section which separates the screen of the monitor into a tracked region which turns ON the tracking function of the tracking device and a non-tracked region which turns OFF the tracking function of the tracking device;
   a selecting device which selects at least one of a first non-tracked region which is positioned generally at the central part of the screen of the monitor and a second non-tracked region which is larger than the first non-tracked region, as the non-tracked region;
   wherein the region separating section switches between the first non-tracked region and the second non-tracked region based on a selection instruction from the selecting device, and when the marker is located in the non-tracked region, the tracking device does not align the position of the marker to the central part of the screen of the monitor.

2. The body cavity interior observing apparatus according to claim 1, wherein the tracking device includes:

a trimming device for trimming an image to obtain a predetermined region so that the position of the marker which is detected by the marker position detecting device is positioned at the central part of the screen of the monitor; and a magnifying device for magnifying the predetermined region trimmed by the trimming device at a predetermined magnification rate to be displayed on the monitor.

3. The body cavity interior observing apparatus according to claim 1, wherein the tracking device calculates a center of gravity of the marker to determine whether the marker is located in the non-tracked region.

* * * * *